United States Patent [19]

Langridge

[11] Patent Number: 5,773,625

[45] Date of Patent: Jun. 30, 1998

[54] PROCESS FOR THE PREPARATION OF DISUBSTITUTED CARBONATES

[75] Inventor: Denton C. Langridge, Wildwood, Ill.

[73] Assignee: Abbott Laboratories, Abbott Park, Ill.

[21] Appl. No.: 942,828

[22] Filed: Oct. 2, 1997

[51] Int. Cl.$^6$ .................. C07D 277/24; C07C 69/76; C07C 205/12

[52] U.S. Cl. .................. 548/203; 548/204; 548/205; 560/61; 560/64; 568/704; 568/826

[58] Field of Search .................. 548/203, 204, 548/205

[56] References Cited

U.S. PATENT DOCUMENTS 5,354,866  10/1994  Kempf et al. .................. 546/265
5,541,206   7/1996  Kempf et al. .................. 514/365

FOREIGN PATENT DOCUMENTS 9616050  5/1996  WIPO .

*Primary Examiner*—José G. Dees
*Assistant Examiner*—Jane C. Oswecki
*Attorney, Agent, or Firm*—Steven R. Crowley

[57] ABSTRACT

The present invention relates to a process for the preparation of cabonate compounds useful for the preparation of compounds which are human immunodeficiency virus (HIV) protease inhibitors.

The compounds have formula I:

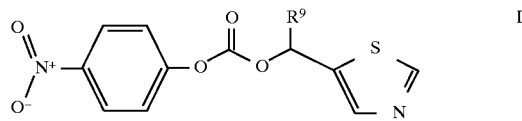

wherein $R^9$ is hydrogen or lower alkyl, and the thiazolyl ring can be unsubituted or substituted with a lower alkyl group.

10 Claims, No Drawings

PROCESS FOR THE PREPARATION OF DISUBSTITUTED CARBONATES

TECHNICAL FIELD

The present invention relates to a process for the preparation of a substituted carbonate compound useful for the preparation of compounds which are human immunodeficiency virus (HIV) protease inhibitors.

BACKGROUND OF THE INVENTION

Compounds which are inhibitors of human immunodeficiency virus (HIV) protease are useful for inhibiting HIV protease in vitro and in vivo and are useful for inhibiting an HIV infection. Certain HIV protease inhibitors comprise a moiety which is a substituted 2,5-diamino-3-hydroxyhexane. HIV protease inhibitors of particular interest are compounds having formula 1:

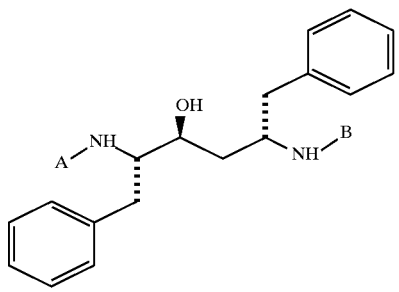

1 wherein A is $R_2NHCH(R_1)C(O)$— and B is $R_{2a}$ or wherein A is $R_{2a}$ and B is $R_2NHCH(R_1)C(O)$— wherein $R_1$ is lower alkyl and $R_2$ and $R_{2a}$ are independently selected from —C(O)—$R_3$—$R_4$ wherein at each occurrence $R_3$ is independently selected from O, S and —N($R_5$)— wherein $R_5$ is hydrogen or lower alkyl and at each occurrence $R_4$ is independently selected from heterocyclic or (heterocyclic)alkyl; or a pharmaceutically acceptable salt, prodrug or ester thereof. Compounds of formula 1 are disclosed in U.S. Pat. No. 5,354,866, issued Oct. 11, 1994, U.S. Pat. No. 5,541,206, issued Jul. 30, 1996, and U.S. Pat. No. 5,491,253, issued Feb. 13, 1996.

A preferred HIV protease inhibitor having formula 1 is a compound of formula 2a:

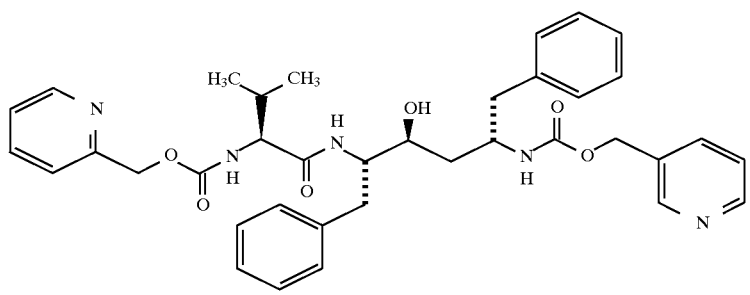

2a or a pharmaceutically acceptable salt, prodrug or ester thereof.

Another preferred HIV protease inhibitor of formula 1 is a compound of formula 2b:

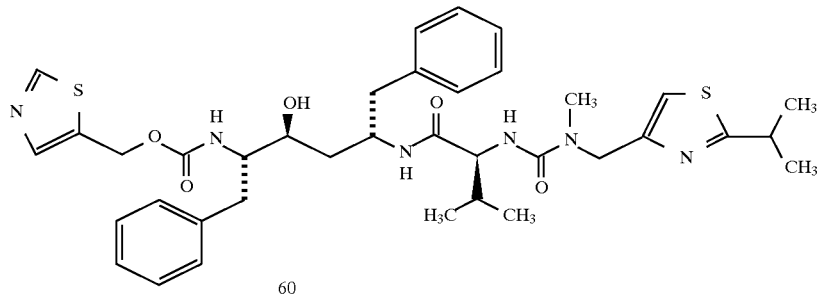

2b

The compound having formula 2b is disclosed in U.S. Pat. No. 5,541,206, issued Jul. 30, 1996.

An intermediate which is especially useful for preparing compounds having formula 1 and 2 is a compound having the formula 3:

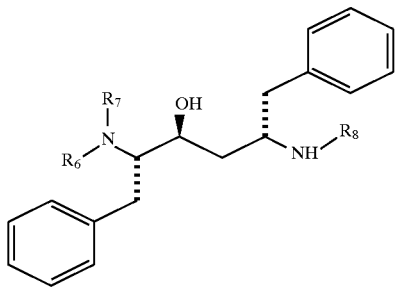

wherein $R_6$, $R_7$ and $R_8$ are independently selected from hydrogen and N-protecting groups, such as, for example, t-butyloxycarbonyl (Boc), benzyl and the like; or an acid addition salt thereof. The preparation of diamino compounds having formula 3 has been disclosed in U.S. Pat. No. 5,491,253, issued Feb. 13, 1996 (the '253 patent).

The compounds of formula 2b or analogs thereof can be prepared by reacting a compound having formula 1 with a disubstituted carbonate compound having formula I

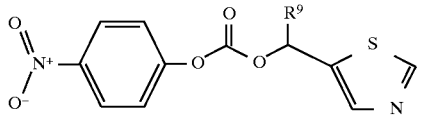

wherein $R^9$ is hydrogen or lower alkyl.

A process for the preparation of compound 1, where $R^9$ is hydrogen, is disclosed in U.S. Pat. No. No. 5,541,206, issued Jul. 30, 1996, (the '206 patent). In the '206 patent a 5-(hydroxymethyl)thiazole (5-HMT) is reacted with 1.5 equivalents of 4-nitrophenyl chloroformate (pNPCF) in an excess of N-methyl morpholine in 100 ml of methylene chloride. After workup the product was purified by silica gel chromatography.

An object of the present invention is to provide a simple method for the preparation of disubstituted compounds having formula 1.

An object of the present Invention is to provide a method for the preparation of disubstituted carbonates which provides these compounds by way of a simple route in high yield.

SUMMARY OF THE INVENTION

The present invention relates to the preparation of a compound having the formula I:

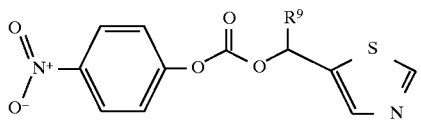

The process comprises reacting a nitrophenyl chloroformate compound having the formula:

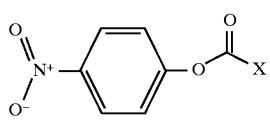

wherein X is a halogen atom, with a thiazole compound having the formula:

in the presence of pyridine. The amount of pyridine present is a catalytic amount. In the present invention, $R^9$ is hydrogen or lower alkyl, and the thiazolyl ring can be unsubstituted or substituted with a lower alkyl group.

The present invention reduces the number of workup steps required for the purification of the final product. This reduction in steps will result in a substantial savings in the final production cost and can increase the yield of product.

All patents, patent applications, and literature references cited in the specification are hereby incorporated by reference in their entirety. In the case of inconsistencies, the present disclosure, including definitions, will prevail.

The preferred halogen atoms, are selected from the group consisting of chlorine and bromine. Preferably, X is chlorine.

The thiazole ring can be unsubstituted or substituted with a lower alkyl substituent.

The term "lower alkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

In the process of the invention the amount of pyridine employed is from about 0.01 to about 0.1 equivalents, based on the number of equivalents of thiazole compound employed. Preferably the amount of pyridine employed is from about 0.05 to about 0.1 equivalents. The most preferred amount of pyridine is from about 0.05 to about 0.07 equivalents The starting material, 5-hydroxymethylthiazole, can be prepared as described in U.S. Pat. No. 5,541,206 and International Patent Application No. WO 96/116050 published May 30, 1996 (the '050 application).

The general process of the invention is illustrated in Scheme I. A solution of 4-nitrophenyl chloroformate, about 1.2 equivalents, and a catalytic amount of pyridine, about 0.01 to about 0.1 equivalents, prepared in an inert solvent, such asethyl acetate (EtOAc) and the like, is maintained at −5° C. A solution of 5-(hydroxymethyl)thiazole in EtOAc is added to the solution . After the addition the reaction mixture is allowed to warm-up to about 5°–6° C. and stirred for at least 24 hours. The solid product is then filtered off and dried.

SCHEME I

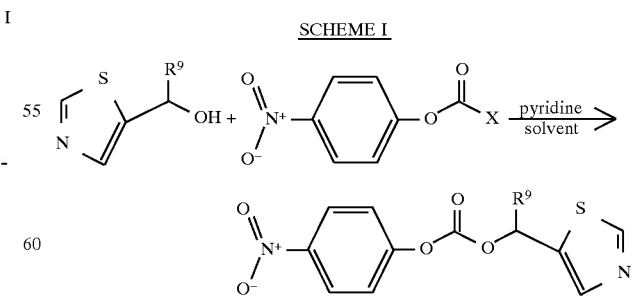

The reaction is considered complete when the amount of 5-HMT remaining is less than about 3% as measured using high performance liquid chromatography (HPLC). The reaction solvent can contain up to about 50% ethanol for the stirred slurry without significant adverse affects. It is important to maintain the reaction temperature at about 5°–6° C. during the reaction and stirring stages of the process. Reactions run at higher temperatures, e.g., 5° C. tend to facilitate a shorter reaction time, but increased levels of impurities are seen at 10° C. Typical yields range from 84 to 95% of theory.

The process of the invention requires that the starting materials be of high purity or the process may be compromised. 4-Nitrophenyl chloroformate (pNPCF) and 5-hydroxymethylthiazole must both be greater than or equal to a BY5/Y5 color as described in British Pharmacopeia, Appendix IV B, pages A107–A108, (1993). The purity of the pNPCF should be greater than 92%. The better the color of pNPCF, i.e., less yellow, the more likely that the product salt will be of acceptable purity without a rework. If a rework is necessary, the type of rework required is chosen based upon the reason the material failed to meet specifications.

The product is tested for purity by HPLC. The product must have greater than 86% of the carbonate compound, less than 10% p-nitrophenol, less than 3% 5-hydroxymethylthiazole, and less than 3% bis-thiazole product If the product does not pass the purity test then the salt product is suspended in ethyl acetate (25 Kg product salt to 150 L ethyl acetate) and washed twice with 1.5 equivalents aqueous 5% potassium carbonate solution per wash. The ethyl acetate product mixture is azeodried (full vacuum, 40°±50° C.) to KF $\leq$0.2%. If necessary, carbon treatment can be utilized after the azeodrying followed by filtration.

The product is converted to the hydrochloride salt by treatment with hydrochloric acid in an inert solvent, such as ethyl acetate and the like (as described in example 3, below). The product salt is then filtered/centrifuged and dried under full vacuum, and nitrogen purge at a temperature of 45°±5° C. to a loss on drying (LOD) of less than 2%.

The reagents required for the synthesis of the compounds of the invention are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA); Alfa Aesar (Ward Hill, Mass. 01835-9953); Eastman Chemical Company (Rochester, N.Y 14652–3512); Lancaster Synthesis Inc. (Windham, N.H. 03087-9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

High performance liquid chromatography (HPLC) was performed using 4.6 mm×150 mm column packed with 100 Å, 5-$\mu$m octadecylsilyl packing (Kromasil, Keystone Scientific Co.) using a variable wavelength UV detector at 205 nm. The mobile phase was acetonitrile/ 0.05M potassium phosphate buffer (45/55 v/v).

The following examples illustrate the process of the invention, without limitation.

EXAMPLE 1

2-Chloro-5-hydroxymethylthiazole (2-Cl-5-HMT)

2-Chloro-5-chloromethylthiazole hydrochloride (10 g, 0.049 mole) and water (100 mL) were charged to a flask. The resultant mixture was stirred at 80° C. for up to but not more than 3 hours. The reaction mixture (about pH=1) was then cooled to room temperature and 10% aqueous sodium carbonate was added. The product was extracted with methyl t-butyl ether (2×100 mL). The combined organic extracts were dried over $Na_2SO_4$ (about 10 g) and stirred for 45 minutes. Optionally, decolorizing carbon can be used. (If a good azeodrying solvent such as ethyl acetate is employed as the extraction solvent a drying agent such as $Na_2SO_4$ is unnecessary.) The solution was then filtered through a fritted glass funnel and the filtrates were concentrated to a yellow colored oil under reduced pressure to provide 2-chloro-5-hydroxymethylthiazole. Yield: 5.65 g, 77.3%.

EXAMPLE 2

2-Chloro-5-hydroxymethylthiazole (2-Cl-5-HMT)

2-Chloro-5-chloromethylthiazole 14.5 g, (0.086 mole) and water (140 mL) were charged to a flask. The resultant mixture was stirred at 80° C. for up to but not more than 3 hours. The reaction mixture (about pH=1) was then cooled to room temperature and sodium carbonate was added to raise the pH of the solution to about 8–9. The product was extracted with ethyl acetate (2×150 mL). The combined organic extracts were dried over $Na_2SO_4$ (about 20 g) and stirred for 45 minutes with 2.0 g of decolorizing carbon (Norit® AS-3 about 100 mesh). The solution was then filtered through a fritted glass funnel and the filtrates were concentrated to a light yellow colored oil under reduced pressure to provide 2-chloro-5-hydroxymethylthiazole. Yield: 12.51 g; 97%.

Results are illustrated below.

$^1$H NMR (CDCl$_3$) d 3.9 (s, broad, 1H), 4.79 (s, 2H), 7.35 (s, 1H). MS(Cl) m/e 150 (M+H)$^+$, 167 (M+NH$^4$)$^+$.

EXAMPLE 3

2-Chloro-5-hydroxymethylthiazole Hydrochloride

2-Chloro-5-chloromethylthiazole hydrochloride (100 g, 0.49 mole), and water (100 mL) were charged to a flask. The mixture was stirred and heated to 80° C. for 2.5 hours. The reaction mixture was cooled to about 15° C. and sodium carbonate (51.5 g) was added (to raise the pH to about 8–9). The product was extracted with ethyl acetate (1×500 mL and 1×250 mL). The combined organic extracts were stirred for 20 minutes with 3 g of decolorizing carbon (Norit® SA3 about 100 mesh) and filtered through celite. The celite and flask were washed with an additional 100 mL of ethyl acetate and combined with the filtrate. The filtrate was concentrated under reduced pressure to provide a yellow-orange oil. The oil was dissolved in 500 mL of ethyl acetate and cooled to −10° C., under a nitrogen atmosphere. A solution of HCl (17.82 grams, 1 eq.) in ethyl acetate was slowly added. The temperature was maintained below −5° C. After the addition was complete the slurry formed was stirred for 30 minutes. The product was filtered under vacuum and the flask and product washed with ethyl acetate (100 mL). The title compound, an off white powder, was purged with nitrogen gas until dry. Yield: 63.3 g; 69.6%.

Results are illustrated below.

$^1$H NMR (CDCl$_3$) d 4.3 (s, broad,1H), 4.83 (s, 2H), 7.45 (s,1H). MS(CI) m/e 150 (M+H)$^+$, 167 (M+NH$^4$)$^+$.

EXAMPLE 4

Preparation of 5-Hydroxymethylthiazole

2-Chloro-5-hydroxymethylthiazole (74.0 g, 495 mmole), was dissolved in methanol (925 mL) and charged into a Parr shaker. To this solution was charged sodium carbonate (26.76 g, 252.5 mmole, 0.51 eq) and 10% palladium on carbon (11.1 g). The system was heated (60° C.) under 50 psi (3.40 atm) of hydrogen gas and agitated for 8 hours. (The reaction mixture can be vented periodically to release the buildup of carbon dioxide gas). The shaker was then cooled and the contents filtered through a bed of diatomaceous earth. The filtrate was then concentrated under reduced pressure (38° C.) and the residue was taken up in methyl t-butyl ether (600 mL) and dried over sodium sulfate (70 g). The dried solution was filtered and concentrated under reduced pressure (38° C.) to provide 5-hydroxymethyl-thiazole. Yield: 52.2 g, 91.6%.

Results are illustrated below.

$^1$H NMR (CDCl$_3$) d 2.9 (broad s,1H), 4.85 (s, 2H), 7.67 (d,1H), 8.70 (s, 1H).

MS (CI) m/e 116 (M+H)$^+$, 133 (M+NH$^4$)$^+$.

EXAMPLE 5

Preparation of 5-Hydroxymethylthiazole

2-Chloro-5-hydroxymethylthiazole hydrochloride (3.72 g, 0.02 mole), was dissolved in methanol (30 mL) and charged into a Parr shaker. To this solution was charged sodium carbonate (2.12 g, 0.02 mole) and 10% palladium on carbon (0.9 g). The system was heated (60° C.) under 50 psi (3.40 atm) of hydrogen gas and agitated for 18 hours. The reaction was monitored by TLC or GC and allowed to proceed for an additional 5 hours after completion. The reaction mixture was cooled and the contents filtered through a bed of diatomaceous earth. The filtrate was then concentrated under reduced pressure (38° C.) and the residue was taken up in methyl t-butyl ether (100 mL) and dried over sodium sulfate (10 g). The dried solution was filtered and concentrated under reduced pressure (38° C.) to provide 5-hydroxymethyl- thiazole as a slightly colored oil. Yield: 2.05 g, 89.1%. The NMR and mass spectral data were identical to the 5-hydroxymethylthiazole product prepared in Example 4.

EXAMPLE 6

Preparation of 5-Hydroxymethylthiazole

2-Chloro-5-hydroxymethylthiazole hydrochloride (3.0 g, 0.02 mole), was dissolved in methanol (30 mL) and charged into a Parr shaker. To this solution was charged triethyl amine (4.09 g, 0.04 mole) and 10% palladium on carbon (0.45 g). The system was heated (57° C.) under 58.8 psi (4.0 atm) of hydrogen gas and agitated for 18 hours. The reaction was monitored by TLC or GC and allowed to proceed for an additional 5 hours after completion. The reaction mixture was cooled and the contents filtered through a bed of diatomaceous earth. The filtrate was then concentrated under reduced pressure and the residue was taken up in methyl t-butyl ether (60 mL) and dried over sodium sulfate (5 g). The dried solution was filtered and concentrated under reduced pressure to provide 5-hydroxymethylthiazole as a slightly colored oil. Yield: 2.1 g, 91.3%. The NMR and mass spectral data were identical to the 5-hydroxymethylthiazole product prepared in Example 4.

EXAMPLE 7

((5-Thiazolyl)methyl)-(4-nitrophenyl)carbonate

A solution comprising 21.0 Kg. (104 mole) 4-nitrophenyl chloroformate dissolved into 75 L ethyl acetate was prepared. The solution was cooled to −5° C. and 0.4 Kg (4 mole) of pyridine dissolved, into 18 L ethyl acetate, was added. The resulting slurry was stirred at −5°±5° C. After 1 hour, 5-hydroxymethyl thiazole 10.0 Kg (87 mole), (HMT) dissolved into 75 L ethyl acetate, was added over 30–40 minutes, maintaining the reaction mixture temperature at −5°±3° C. The resulting slurry was then warmed to 0°±5° C., and stirred for at least about 24 hours. The reaction was checked for completion by HPLC. Upon completion, absolute ethanol, 32 Kg, was added to the slurry (about 15–20% of the total reaction volume), stirred for at least about 2 hours, and then centrifuged or filtered. The product solid was washed with cold ethyl acetate (2×75 L) and dried at 40°±5° C. to an LOD <2%. Yield: 25.15 Kg (93%).

Results are illustrated below.

$^1$H NMR (CDCl$_3$) d 5.53 (s, 2H), 7.39 (dt, J =9, 3 Hz, 2H), 8.01 (s, 1H), 8.29 (dt, J =9, 3 Hz, 2H), 8.90 (s, 1H). Mass spectrum: (M+H)$^+$=281.

COMPARATIVE EXAMPLE 7

((5-Thiazolyl)methyl)-(4-nitrophenyl)carbonate

A solution of 3.11 g (27 mmole) of 5-(hydroxymethyl) thiazole and excess N-methyl morpholine in 100 ml of methylene chloride was cooled to 0° C. and treated with 8.2 g (41 mmole) of 4-nitrophenyl chloroformate. After being stirred for 1 h, the reaction mixture was diluted with CHCl$_3$, washed successively with 1N HCl, saturated aqueous NaHCO$_3$, and saturated brine, dried over NaSO$_4$, and concentrated in vacuo. The residue was purified by silica gel chromatography (SiO$_2$, 1–2% MeOH/CHCl$_3$, Rf=0.5 in 4% MeOH/CHCl$_3$) to provide the desired compound as a yellow solid. Yield: 5.9 g, 78%. The NMR and mass spectral data were identical to the ((5-thiazolyl)-methyl)-(4-nitrophenyl) carbonate product prepared in Example 7.

The foregoing is merely illustrative of the invention and is not intended to limit the invention to the disclosed processes and reaction conditions. Variations which are obvious to one of ordinary skill in the art are intended to be included within the scope and nature of the invention which are defined in the appended claims.

What is claimed is:

1. A process for the preparation of a compound having the formula:

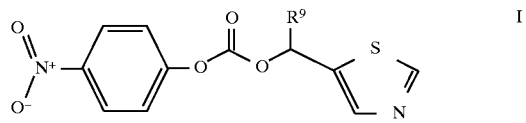

wherein said process comprises reacting a nitrophenyl chloroformate compound having the formula:

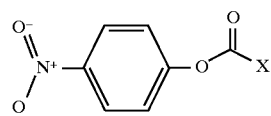

wherein X is a halogen atom, with a hydroxymethylthiazole compound having the formula:

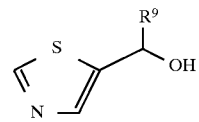

wherein the thiazolyl ring is unsubstituted or substituted with a lower alkyl group; in the presence of pyridine, and wherein the pyridine is present in a catalytic amount;

wherein R⁹ is hydrogen or lower alkyl.

2. The process according to claim 1, wherein the amount of pyridine is from about 0.01 to about 0.1 equivalents, based on the number of equivalents of hydroxymethylthiazole compound.

3. The process according to claim 1, wherein the amount of pyridine is from about 0.05 to about 0.1 equivalents, based on the number of equivalents of hydroxymethylthiazole compound.

4. The process according to claim 1, wherein the amount of pyridine is from about 0.05 to about 0.07 equivalents, based on the number of equivalents of hydroxymethylthiazole compound.

5. The process according to claim 1, wherein X is selected from the group consisting of chlorine and bromine.

6. The process according to claim 3, wherein X is chlorine.

7. The process according to claim 1, wherein thiazolyl ring is unsubstituted.

8. The process according to claim 1, wherein thiazolyl ring is substituted with a lower alkyl group.

9. The process according to claim 1, for the preparation of a compound having the formula:

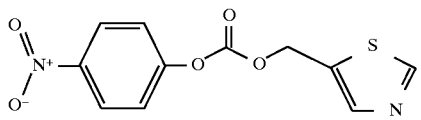

wherein said process comprises reacting a nitrophenyl chloroformate compound having the formula:

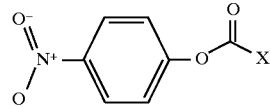

wherein X is a halogen atom, with a hydroxymethylthiazole compound having the formula:

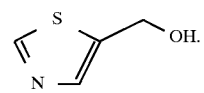

10. The process according to claim 1, wherein X is chlorine and R⁹ is hydrogen.

* * * * *

UNITED STATES PATENT AND TRADEMARK OFFICE
CERTIFICATE OF CORRECTION

PATENT NO. : 5,773,625
DATED : June 30, 1998
INVENTOR(S) : Langridge

It is certified that error appears in the above-identified patent and that said Letters Patent is hereby corrected as shown below:

Abstract, line 2, change "cabonate" to --carbonate--.

Abstract, last line, change "unsubituted" to --unsubstituted--.

Signed and Sealed this

Tenth Day of November 1998

Attest:

BRUCE LEHMAN

Attesting Officer                    Commissioner of Patents and Trademarks